United States Patent [19]

Funahashi et al.

[11] 4,158,002

[45] Jun. 12, 1979

[54] PROCESS FOR PREPARING DINITROAZO- (OR AZOXY-)BENZENE

[75] Inventors: Kazutoshi Funahashi; Yoichi Saito, both of Hino, Japan

[73] Assignee: Teijin Limited, Osaka, Japan

[21] Appl. No.: 899,866

[22] Filed: Apr. 25, 1978

Related U.S. Application Data

[63] Continuation-in-part of Ser. No. 735,945, Oct. 27, 1976, abandoned.

[30] Foreign Application Priority Data

Oct. 31, 1975 [JP] Japan .............................. 50-130346
Dec. 24, 1975 [JP] Japan .............................. 50-153352

[51] Int. Cl.² ................. C07C 105/00; C07C 107/06; C07C 85/11
[52] U.S. Cl. ........................... 260/143; 260/205; 260/578; 260/580; 260/582
[58] Field of Search ............... 260/580, 578, 143, 205

[56] References Cited

U.S. PATENT DOCUMENTS

| | | | |
|---|---|---|---|
| 1,882,758 | 10/1932 | Britton et al. | 260/578 |
| 1,890,430 | 12/1932 | Perkins et al. | 260/578 |
| 1,998,488 | 4/1935 | Calcott et al. | 260/578 |
| 3,063,980 | 11/1962 | Bloom et al. | 260/205 |

OTHER PUBLICATIONS

Ginsburg, "Concerning Amines," pp. 18 & 19, (1967).
Sidgwick, "The Organic Chemistry of Nitrogen," p. 586, (1966).
Fierz-David, "Fundamental Processes of Dye Chemistry," pp. 69, 70 & 72, (1949).
Augustine, "Catalytic Hydrogenation," pp. 91–93 & 95, (1965).
Green et al., "J. Chem. Soc.," vol. 101, pp. 2443–2452, (1912).
Zollinger, "Azo and Disazo Chemistry," p. 292, (1961).
Sharnin et al., "J. Chem. Soc. USSR," vol. 10(4), pp. 1489–1492, (1970).

*Primary Examiner*—Patrick Garvin
*Assistant Examiner*—John Doll
*Attorney, Agent, or Firm*—Sherman & Shalloway

[57] ABSTRACT

A process for preparing a compound of the formula

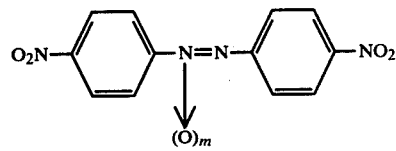

wherein m represents zero or 1, which comprises reacting azobenzene with nitric acid in the presence of sulfuric acid in two steps, wherein
(1) the first-step reaction is carried out under the following conditions $0 < x \leq 80$, $0 < y \leq 11$, and $-0.3x + 12 \leq y \leq -0.22x + 22$ wherein x is the reaction temperature in °C., and y is the weight ratio of sulfuric acid to water and fed into the reaction system, and
(2) the second-step reaction is carried out under the following conditions $0 \leq x$, and $-(1.7/100)x + 1.7 \leq y \leq -(3.9/88)x + 3.9$.

5 Claims, 3 Drawing Figures

Fig. 2
4-nitroazobenzene → 4,4'-dinitroazobenzene

Fig. 1
azobenzene → 4-nitroazobenzene

Fig. 3

PROCESS FOR PREPARING DINITROAZO- (OR AZOXY-)BENZENE

This application is a continuation-in-part application of Ser. No. 735,945 filed on Oct. 27, 1976, now abandoned.

This invention relates to a process for producing polyamino-substituted benzene by the reductive hydrogenation of nitro-substituted azobenzene or azoxybenzene, and a process for producing the starting nitro-substituted azobenzene or azoxybenzene.

Polyamino-substituted benzenes, particularly p-phenylenediamine, find a wide range of commercial applications. For example, they are useful as materials for the preparation of thermally stable polymers, color-formers in photography, materials for dyes and pigments, and anti-oxidants for rubbers.

According to the prior art, p-phenylenediamine is synthesized by various methods, for example, the reduction of p-nitroaniline with iron-hydrochloric acid, the ammonolysis of p-dichlorobenzene, the reductive hydrogenation of p-dinitrobenzene, or the Hofmann degradation of terephthalamide. Furthermore, U.S. Pat. No. 2,708,680 suggested the hydrogenation of 4-aminoazoenzene with iron hydrochloric acid, and JACS 56 1411 (1934) suggested the hydrogenation of 4-aminoazobenzene using platinum or nickel as a catalyst. These methods, however, are not effective both economically and in separating the resulting product because aniline is formed as a by-product in the same molar amount as the desired p-phenylenediamine from the starting 4-aminoazobenzene.

Helv. Chim. Acta 30 735 (1947) reported that p-phenylenediamine is obtained by hydrogenating 4-nitroazo-benzene using a Raney nickel catalyst. This method is neither effective because aniline is formed as a by-product in the same molar amount as p-phenylenediamine.

Berichte d. D. Chem. Gesellschaft 5 235 (1972) disclosed that p-phenylenediamine is produced by heating 4,4'-dinitroazobenzene to 100° C. in a sealed tube using ammonium sulfide. However, as ammonium sulfide is used in this method, it is time-consuming and troublesome to separate and purify the resulting p-phenylenediamine. In addition, this reaction yields sulfur compounds whose disposal poses a problem in view of pollution control.

A method is known to produce the nitro-substituted azobenzene or azoxybenzene, the starting compound for preparing the polyamino-substituted benzene, for example the compound of the formula (I)

wherein m represents a number of 0 or 1.

For example, they can be prepared by a method which starts from p-nitroaniline and goes through a diazonium salt (Green et al., "J. Chem. Soc." vol. 101, pp. 2443–52 (1912)). They can also be prepared by the method reported in Berichte d. D. Chem. Gesellschaft 32, 3256 (1899) and J. Chem. Soc. 1953, 2150 which comprises reacting azobenzene with fuming nitric acid to form 4,4'-dinitroazobenzene.

However, since the reaction route through a diazonium salt is long and complicated, it is quite infeasible for industrial application. When fuming acid is used, the reaction is extremely difficult to control, and large amounts of unwanted polynitro compounds are formed, and the handling of the fuming acid requires great care.

It is an object of this invention therefore to provide a practical process for producing 4,4'-dinitroazobenzene easily in a high yield by nitrating azobenzene.

Another object of this invention is to provide a process for producing 4,4'-dinitroazobenzene by nitrating azobenzene, which is substantially free from the need to discharge the spent acids from the reaction system.

These objects can be achieved in accordance with this invention by a process for producing a compound of the formula wherein m represents zero or 1, which comprises reacting azobenzene with nitric acid in the presence of sulfuric acid in two steps, wherein (1) the first step reaction is carried out under the following conditions $$0 < x \leq 80,$$

$$0 < y \leq 11, \text{ and}$$

$$-0.3x \times 12 \leq y \leq -0.22x + 22$$

wherein x is the reaction temperature in °C., and y is the weight ratio of sulfuric acid to water fed into the reaction system ($H_2SO_4/H_2O$ ratio), and (2) the second step reaction is carried out under the following conditions $$0 \leq x, \text{ and}$$

$$-(1.7/100)x + 1.7 \leq y \leq -3.9/88x + 3.9.$$

It has been the general common knowledge that when nitrobenzene is further nitrated to form dinitrobenzene, the nitro group is introduced meta to the first nitro group. In view of this, it is surprising that in the two-step process of the invention, nitration in the second step gives 4,4'-dinitroazobenzene easily in a high yield.

The resulting 4,4'-dinitroazobenzene can be used to prepare useful p-diaminobenzene by hydrogenolysis.

One preferred embodiment of the reaction in accordance with this invention comprises dissolving or suspending the starting nitro-substituted azobenzene and/or nitro substituted azoxybenzene in a suitable solvent, adding a hydrogenating catalyst to form a reaction solution, and contacting it with hydrogen with stirring at a predetermined temperature. Alternatively, the solution may be reacted with hydrogen at high pressures in a pressure reactor.

The hydrogenating catalyst used in the process of this invention is required to have a dual activity of reducing the nitro groups in the nitro-substituted azobenzene to amino groups and hydrogenatingly cleaving the azo and/or azoxy groups to amino groups. Many common hydrogenating catalysts meet this requirement, and they include, for example, platinum group metals, nickel, cobalt, copper, rhenium, and iridium. Specific examples are platinum black, colloidal platinum, platinum oxide, palladium black, palladium-on-carbon, palladium oxide, colloidal palladium, reduced nickel, Raney nickel, rhenium black, colloidal iridium, copper-chromium oxide, molybdenum oxide, and cobalt-chromium oxide. Of these, the platinum-group metals and nickel are especially effective.

Increasing the surface area of the catalyst by depositing it on a carrier is sometimes effective for increasing the rate of reaction, and in many cases, the use of catalyst carriers is desirable. Examples of the carrier are alumina, silica gel, diatomaceous earth, activated earths, asbestos, magnesium oxide, zinc oxide, chromium oxide, and barium carbonate.

These catalysts and carriers can be used either alone or in admixture of two or more.

The larger the amount of the catalyst used in the present invention, the more advantageous it is to increase the rate of reaction. But the amount is determined according to the type of the catalyst, the reaction conditions, and the reaction operations, and generally, suitable amounts used in this invention are 0.1 to 30% by weight based on the nitro-substituted azobenzene and/or nitro-substituted azoxybenzene. This range of amounts, however, is not critical.

The solvent used in the present invention is required to be stable, and does not undergo a reaction such as hydrogenation, under the reaction conditions. Solvents meeting this requirement can be used in many cases, but those which dissolve the starting nitro-substituted azobenzene and/or nitro-substituted azoxybenzene are more preferred. When water or a mixture of it with another solvent is used as the solvent in accordance with this invention, unwanted side-reactions may sometimes occur under strongly acidic conditions, and therefore, care should be taken in this regard. Usable solvents are, for example, water, methanol, ethanol, dioxane, tetrahydrofuran, benzene, ether, acetic acid, ethyl acetate, and dimethyl formamide.

Hydrogen used in this invention is molecular hydrogen produced industrially in great quantities. In order to perform the reaction, hydrogen is charged into a vessel containing the starting nitro-substituted azobenzene and/or nitro-substituted azoxybenzene, the hydrogenation catalyst and the solvent. The pressure of the hydrogen charged differs according to the type of the hydrogenation catalyst, the reaction temperature, and the weight of the charged material, but is conveniently 1 to 150 atmospheres. This range, however, is not critical. Generally, higher pressures of hydrogen are desirable in order to increase the rate of reaction. Hydrogen may be charged at a time in an amount sufficient for reduction. Alternatively, it is supplementally added with the progress of the reaction in an amount corresponding to the amount consumed, or in an amount larger or smaller than the amount consumed.

The reaction temperature employed in the present invention varies according, for example, to the type of the hydrogenation catalyst used, or the pressure of hydrogen, but generally ranges from 10° to 300° C. This range is not critical, however. When the reaction temperature is too low, the reaction is slow, or stops at a point where an intermedite has been formed. Or it does not proceed at all. On the other hand, if the reaction temperature is too high, undesired compounds such as products obtained by hydrogenation of the aromatic ring, or diarylamines are formed as by-products.

The end point of the reaction can generally be determined by a decrease in the amount of hydrogen charged. Specifically, the absorption of a stoichiometric amount is measured in terms of the volume of absorption in a reaction at atmospheric pressure, and by the decreasing pressure of a pressure gauge in a reaction at an elevated pressure.

One of the advantages of the process of the invention is that since it is a catalytic hydrogenation process, the separation of the resulting diaminobenzene or triaminobenzene from the reaction mixture is easy. In many cases, the diaminobenzene or triaminobenzene can be separated and purified by a generally used method such as distillation and recrystallization after separating the catalyst from the reaction mixture.

Another preferred embodiment of the reaction in the present invention comprises dissolving or suspending the starting nitro-substituted azo- (or azoxy-)benzene in an aqueous solvent containing hydrochloric acid, and reacting it at a predetermined temperature after adding iron or zinc.

The hydrochloric acid used in this embodiment is of a grade generally used. The amount of the hydrochloric acid is suitably 0.2 to 6 mole equivalents based on the azo- (or azoxy-)benzene, but is not limited to it. However, if it is too small, the rate of reaction becomes slow, and in some cases, the reaction does not sufficiently proceed but stops at the stage of an intermediate. If it is too large, the separation of the resulting diaminobenzene or triaminobenzene is time-consuming. Furthermore, the proportion of by-products increases, and in some case, the final compound can hardly be obtained. The initial concentration of the acid in the reaction system is about 0.08 to 0.8 N. If the concentration of the acid is outside this range, the formation of diaminobenzene or triaminobenzene is generally poor or not appreciable.

In this embodiment, water is used as a reaction solvent. It is generally convenient, however, to add another solvent in order to increase the solubility of the starting nitro-substituted azo- (or azoxy-)benzene and the rate of reaction.

Solvents which are stable in the reaction system, do not hamper the reaction, and are miscible with water are more convenient. Alcohols and aniline are especially preferred as such solvents.

Iron and zinc used in the reaction are more advantageous in regard to the rate of reaction when they are in the form of powder. The amount of iron or zinc used is 6 to 35 mole equivalents based on the azobenzene, but is not limited to this range. If, however, it is too small, the rate of reaction decreases, or it becomes difficult to complete the reaction. If it is too large, it is time-consuming to separate the resulting diaminobenzene or triaminobenzene from the reaction mixture. Part of the iron powder may be replaced by iron chloride in carrying out the reaction.

The reaction temperature used in this invention is desirably 50° to 100° C., but not limited to this range.

The diaminobenzene or triaminobenzene formed can be separated from the reaction mixture by chemical and physical separating and purifying methods generally employed. For example, the resulting diamino- or triaminobenzene can be recovered by neutralizing the free hydrogen chloride or hydrogen chloride forming a salt with the diamino- or triaminobenzene with an alkali after the reaction, separating a greater portion of the iron compound by filtration, extracting the resulting solution with a solvent after removing the solvent from it or without removing it, and then distilling the residue.

A process for forming the nitro-substituted azo- or azoxy-benzene of formula (I) in this invention is a method comprising reacting azobenzene with mixed acid in two steps. Specifically, it comprises nitrating azobenzene with nitric acid in the presence of sulfuric acid to afford 4-nitroazobenzene first, and 4,4'-dinitroazobenzene and 4,4'-dinitroazoxybenzene finally. In the reaction of the second step, 1 to 50 mole equivalents of nitric acid is used based on the 4-nitroazobenzene. Nitric acid having a concentration corresponding to a specific gravity of 1.12 to 1.52 is conveniently used in this case. The sulfuric acid is used in an amount of 0.3 to 2.0 mole equivalents based on the nitric acid. The sulfuric acid used generally has a specific gravity of 1.8. The reaction is carried out at a temperature of 0° to 80° C., but may be varied according to the concentrations of nitric acid and sulfuric acid, and the ratio of these acids to the starting 4-nitroazobenzene. However, when the reaction temperature is low, the reaction is slow. When it is high, by-products are formed in increased quantities. The final product is obtained by separating the precipitate in the reaction mixture by filtration.

The reaction conditions should be selected according to which of 4,4'-dinitroazobenzene, and the corresponding azoxybenzene compounds is to be obtained as the main desired product. When 4,4'-dinitroazobenzene is synthesized from 4-nitroazobenzene using mixed acid, 4 to 40 mole equivalents of sulfuric acid is used based on the 4-nitroazobenzene, and sulfuric acid is used in an amount of 0.3 to 2.0 mole equivalents based on nitric acid. The reaction temperature is 0° to 80° C. when the 4,4'-dinitroazobenzene is desired.

The amount of nitric acid used in the second step depends upon the amount of 4-nitroazobenzene formed by the first-step reaction and the amount of the unreacted azobenzene. Let $M_1$ be the moles of nitric acid, $M_2$ the moles of the 4-nitroazobenzene fed and $M_3$ the moles of the unreacted azobenzene, then the preferred amount of nitric acid used in the second step is $$1 \leq M_1/(M_2+2M_3) \leq 50$$

and the more preferred amount is $$3 \leq M_1/(M_2+M_3) \leq 30$$

The ratio of nitric acid to 4-nitrobenzene and azobenzene in the second step is higher than the ratio of nitric acid to azobenzene in the first step because the ease of introduction of a nitro group into 4-nitroazobenzene is less.

By starting from 4-nitroazobenzene to produce a compound of formula (I), the yield of the product markedly increase over the case of synthesizing it in a single step starting from azobenzene. That is because there is a difference between the conditions for forming mononitro compounds and those for forming polynitro compounds.

Whatever compound may be finally desired, some amounts of other nitro-substituted azo- and azoxy-benzene compounds are inevitably formed as by-products. For example, when the main desired compound is 4,4'-dinitroazobenzene, the reaction product will contain by-products such as 4,4'-dinitroazoxybenzene, 4-nitroazobenzene and 4-nitroazoxybenzene.

In the first step, the concentration of nitric acid used is one corresponding to a specific gravity of 1.12 to 1.47. The concentration of nitric acid is affected by the reaction temperature and the contents of sulfuric acid in the reaction system. The proportion of nitric acid based on the azobenzene is 0.5 to 1.5, preferably 0.7 to 1.2 mole equivalents. Even when nitric acid is used in an excessive amount with respect to azobenzene which is within the aforesaid range of the amount of nitric acid, the nitric acid is substantially consumed in the first-step reaction of this invention. This is because the excess of the nitric acid can convert part of azobenzene to 4,4'-dinitroazobenzene. If the proportion of nitric acid is too small, the reaction does not proceed at a sufficient speed, but the ratio of the unreacted material increases. On the other hand, if it is too large, the operation is troublesome in treating the excess of nitric acid.

The amount of sulfuric acid used is 0.1 to 1.0 mole equivalent based on the nitric acid. Generally, the rate of nitration increases by adding sulfuric acid. If the amount of sulfuric acid is larger, the azoxy compound is formed in an increased amount. This compound can however be used also as a starting compound in the reductive hydrogenation in accordance with this invention.

The nitration of the azobenzene can be carried out at a reaction temperature of 0° to 80° C. The preferred range of the reaction temperature is determined, however, according to other reaction conditions such as the concentrations of nitric acid and sulfuric acid and the proportions of these based on the starting material. There is a general tendency that the rate of reaction is slower at lower reaction temperatures, and higher reaction temperatures tend to form increased amounts of by-products. The product can be separated by filtering the precipitate in the reaction mixture. Sometimes, the separation becomes easier by pouring water into the reaction mixture. The resulting product contains 4-nitroazobenzene as a main ingredient. If required, this compound is further purified, and nitrated to form a dinitrated compound of formula (I).

In order to convert the 4-nitroazobenzene obtained by the nitration of azobenzene to the dinitro compound of formula (I), sulfuric acid and if required, nitric acid are added to the reaction mixture containing 4-nitroazobenzene in the reactor at the end of the reaction without separating the 4-nitrobenzene from it. Alternatively, this can be achieved by changing the reaction conditions, for example, the reaction temperature.

When azobenzene is nitrated with nitric acid containing sulfuric acid to form 4-nitroazobenzene, the nitric acid containing sulfuric acid may be one which is left after the separation of the final product in the preparation of the dinitroazo- (or azoxy-)benzene of formula (I) by reacting 4-nitroazobenzene with mixed acid as described above. According to such a method, a reaction of converting azobenzene to 4-nitroazobenzene by nitration (first-step nitration reaction) and a reaction of converting the 4-nitroazobenzene obtained by the first-step nitration reaction to the dinitroazo- or azoxybenzene of formula (I) by nitration (second-step nitration reaction) may be carried out successively in one system. This can afford the compound of formula (I) from azobenzene through 4-nitroazobenzene without the need to discharge the spent acid outside the system.

The accompanying drawings are graphs showing the relation between the reaction temperature and the $H_2SO_4/H_2O$ weight ratio in the first-step reaction (FIG. 1) and the second-step reaction (FIG. 2), in which the reaction temperature is shown on the axis of abscissas and the $H_2SO_4/H_2O$ ratio on the axis of ordinates.

Figure 1:
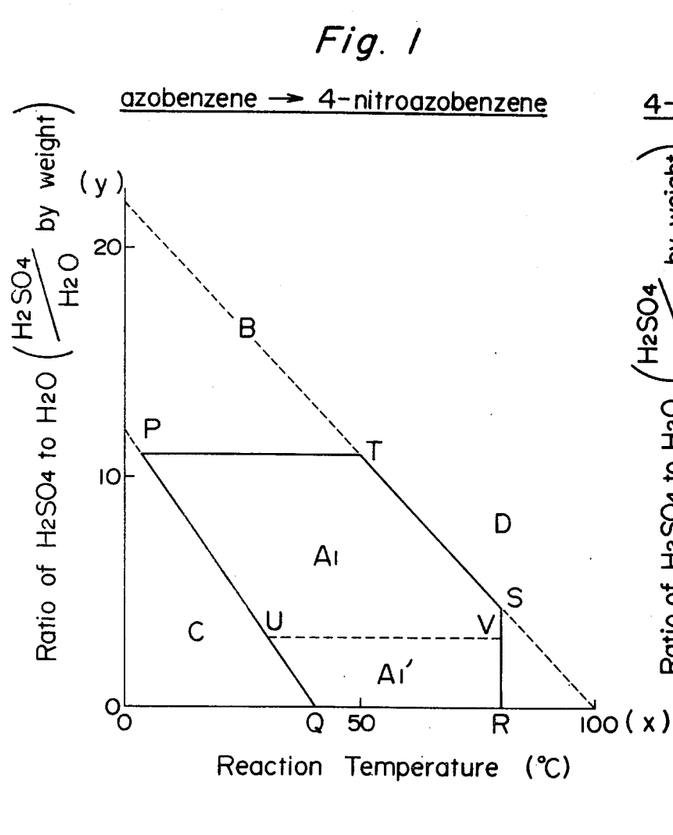

In the first-step reaction of this invention to produce 4-nitroazobenzene from azobenzene, the reaction temperature (x° C.) and the $H_2SO_4/H_2O$ weight ratio (y) should be in the following relation:

$0 < x \leq 80$, $0 < y \leq 11$, and $-0.3x + 12 \leq y \leq -0.22x + 22$.

This relation corresponds to regions $A_1 + A'_1$ surrounded by lines PQ, QR, RS, ST and TP in FIG. 1.

The preferred relation between x and y is:

$0 < x \leq 80$, $0 < y \leq 3$, and $-0.3x + 12 \leq y \leq -0.22x + 22$.

This relation corresponds to the region $A'_1$ surrounded by lines UQ, QR and RV and dotted line VU in FIG. 1.

Outside this region, the yield of 4-nitroazobenzene decreases. In region B in which the concentration of sulfuric acid is higher, the nitration action is strong as is the case with fuming nitric acid, and even at a low temperature, 2,4,4'-trinitroazobenzene or 2,4,4'-trinitroazoxybenzene is liable to form and the control of the reaction is difficult.

In region C in which both the temperature and the $H_2SO_4/H_2O$ weight ratio are low, the reaction does not proceed sufficiently, and in many cases, the starting material is recovered unchanged. In region D where the temperature is high, azoxy compounds are liable to form, and azoxybenzene, 4-nitroazoxybenzene and other high oxidation state by-products tend to occur.

When the first-step reaction and the second-step reaction are carried out in a single closed circuit, it is preferred to employ the conditions within region $A'_1$.

Figure 2:
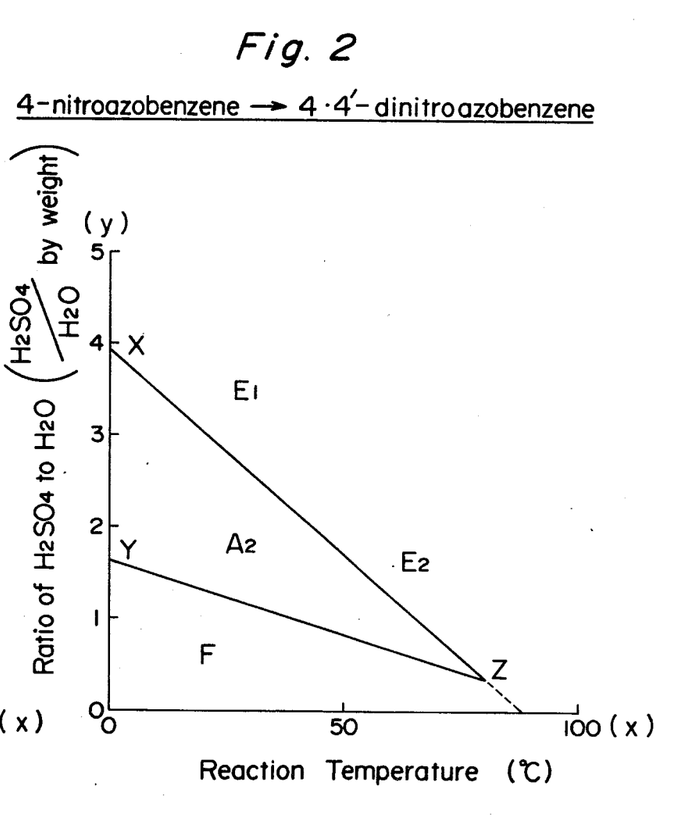

In the second-step reaction of producing 4,4'-dinitroazobenzene from 4-nitroazobenzene, x and y should be in the following relation:

$0 \leq x$, and $-(1.7/100)x + 1.7 \leq y \leq -(3.9/88)x + 3.9$

This relation corresponds to region $A_2$ surrounded by lines XY, XZ and ZX in FIG. 2. Outside this region, the yield of 4,4'-dinitroazobenzene is low. In region $E_1$, the concentration of sulfuric acid to too high and the nitrating action is too strong. Hence, 2,4,4'-trinitroazobenzene is liable to form and the temperature is difficult to control. In region $E_2$, other undesirable by-products occur. In region F, the concentration of sulfuric acid and the temperature are low, and the reaction does not proceed sufficiently.

In the present invention, nitration reaction can be performed in high yields by using the conditions in regions $A_1$, $A'_1$ and $A_2$. By using the conditions within the regions $A'_1$ and $A_2$, the acids used in the first-step and second-step reactions can be efficiently recycled.

Figure 3:
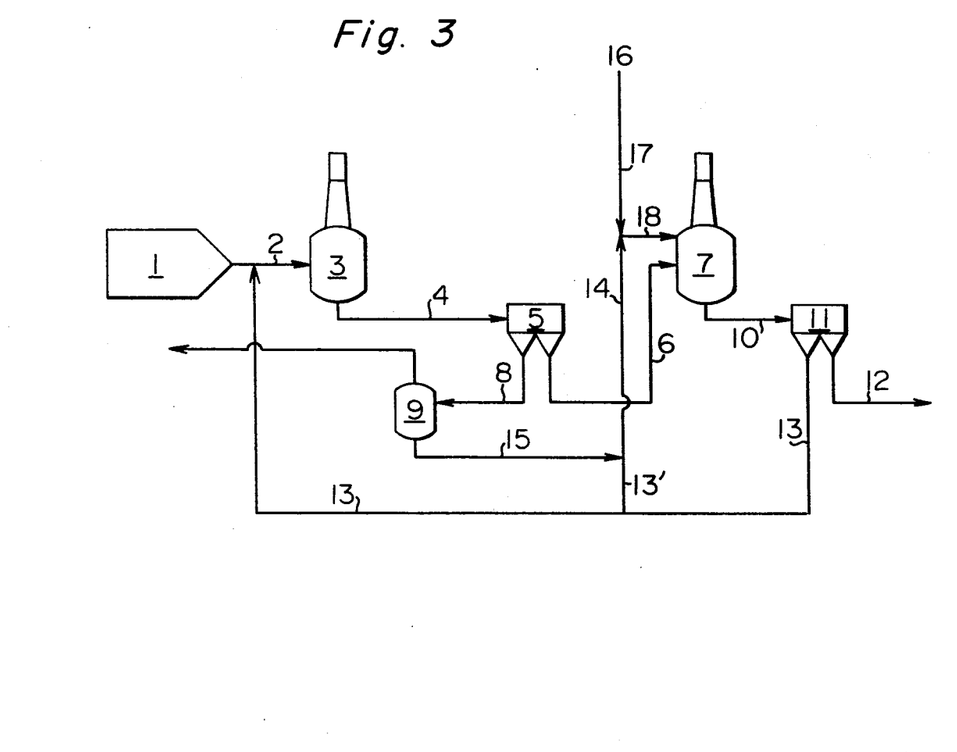

One example of this reaction system is shown in FIG. 3 which is a flow chart accompanying the present application.

In FIG. 3, the starting azobenzene 1 passes through a line 2 and enters a first-step nitration reactor 3 together with a stream of the spent acid (mixture of nitric acid and sulfuric acid) which has come from a separator 11 for separating the product of the second-step nitration reaction through a line 13. The azobenzene is converted to 4-nitroazobenzene in the reactor 3. The first-step nitration reaction product is sent to a separator 5 through a line 4, in which the 4-nitroazobenzene as the first-step reaction product is separated from the spent acid. The 4-nitroazobenzene separated is sent to a second-step nitration reactor 7 through a line 6. In the meantime, the spent acid is fed into a tank 9 for concentrating sulfuric acid. This spent acid contains substantially no nitric acid since the nitric acid has been consumed in the first-step nitration reaction.

The 4-nitroazobenzene separated by the separator 5 is sent to the second-step nitration reactor 7 through the line 6. Also, fresh nitric acid 16, the spent acid (mixture of nitric acid and sulfuric acid) from the separator 11, and the spent sulfuric acid concentrated in the concentration tank 9 are fed into the second-step reactor 7 through a line 17, lines 13 and 13', and a line 15, respectively. Thus, in the reactor 7, the second-step nitration is performed. The product from the second-step nitration enters the separator 11 through a line 10, and separated into the desired product of formula (I) and the spent acid. The final desired product is withdrawn through a line 12, and the spent acid is flowed dividedly through the line 13 and 13'. The divided flows of the spent acid are recycled to the first-step nitration reactor 3 and the second-step nitration reactor 7, respectively.

In the reaction system described above, evaporated water discharged from the sulfuric acid concentrating tank through line 19 and the final product withdrawn from the line 12 go outside the reaction system, but the spent acid is recycled and not discharged out of the system.

In order to perform the operation conveniently in such a recycle system, the mixed acid preferably consists of 10 to 70% by weight of sulfuric acid, 10 to 55% by weight of water and 1 to 70% by weight of nitric acid in the first-step reaction, and of 10 to 65% by weight of sulfuric acid, 10 to 30% by weight of water and 20 to 80% by weight of nitric acid in the second-step reaction.

The reaction is carried out by adding azobenzene to nitric acid and sulfuric acid, and stirring the mixture at a predetermined temperature to be described. In order to increase the stirring effect, another solvent may be added. For this purpose, solvents which do not react with nitric acid and sulfuric acid in this reaction system, for example, acetic acid are used. The product is recovered by separating the precipitate in the reaction mixture by filtration.

Whatever compound may be the main desired compound, other nitrated azo- and azoxy-benzene compounds are formed in some amounts as by-product. For example, when the main final product is 4,4'-dinitroazobenzene, the product also contains 4,4'-dinitroazoxybenzene, 4-nitroazobenzene, and 4-nitroazoxybenzene as by-products.

The method for nitrating azobenzene in accordance with this invention have various advantages among which are:

1. the use of mixed acid for nitration of the azobenzene nucleus has made it possible (1) to control the reaction easily, and to (2) consume nitric acid effective or completely for the nitration, and
2. the yield of the product can be markedly increased as a result of carrying out the nitration in two steps.

The following examples illustrate the present invention in greater detail. All "parts" in these examples are by weight unless otherwise specified.

The gas chromatographic analyses were carried out under the following conditions unless otherwise stated.

| | |
|---|---|
| Filler: | polyethylene glycol 20 M, ratio of impregnation 10% |
| Carrier: | Diasolid L (a kind of diatomaceous earth; a product of Nippon Chromato Kogyo K.K.) |
| Column length: | 1 m |
| Column inside diameter: | 3 mm |
| He flow rate: | 55 ml/min. |
| Column temperature: | 220° C. |
| Maintenance time: | p-Phenylenediamine 3 minutes α-methylnaphthalene (internal reference) 35 seconds |

EXAMPLES 1 AND 2

A 200-ml glass reactor equipped with a gas-introducing tube and fixed on a shaking vessel was charged with 3.4 g of 4,4'-dinitroazobenzene, 50 ml of ethanol and each of the hydrogenation catalysts shown in Table 1. The inside of the reactor was purged completely with hydrogen, and the reaction was carried out with shaking at 80° C. for 4 hours while introducing hydrogen at normal atmospheric pressure from a gas holder. The reaction was terminated when the reaction mixture no longer absorbed hydrogen. The reaction mixture was filtered. The cake was washed with ethanol. The filtrate and the wash liquid were analyzed gas-chromatographically for the determination of p-phenylenediamine. The identification and determination of the product were carried out by comparing the gas-chromatogram of the filtrate with that of a standard product.

The solvent was removed from the filtrate in an atmosphere of nitrogen, and the residue was recrystallized from benzene to afford crystals having a melting point of 143° to 144° C. The IR spectrum of the purified p-phenylenediamine completely corresponded with that of a standard product. The results of the reaction are shown in Table 1.

Table 1

| | Catalyst | | Yield (%) of p-phenylene-diamine | Yield of the recrystallized product (%) |
|---|---|---|---|---|
| Example | Type | Amount (g) | | |
| 1 | Pd-C (5% of Pd) | 0.3 | 98 | 94 |
| 2 | PtO | 0.3 | 96 | 92 |

EXAMPLES 3 TO 10

A 100 ml pressure reactor equipped with a stirrer, a pressure gauge and a gas-introducing tube was charged with 1.7 g of 4,4'-dinitroazobenzene, 25 ml of each of the solvents shown in Table 2 and each of the hydrogenation catalysts shown in Table 2 in the amounts indicated. The air-tight inside of the reactor was purged with nitrogen, and hydrogen at a predetermined pressure was introduced from the gas-introducing tube. The reactor was maintained at each of the predetermined pressures shown in Table 2, and the reaction was carried out with stirring. The determination and identification of the resulting p-phenylenediamine were carried out in accordance with the procedure set forth in Example 1. The results are shown in Table 2.

Table 2

| | | | | Reaction conditions | | | Yield (%) of |
|---|---|---|---|---|---|---|---|
| Example | Type | Amount (g) | Solvent | Temp. (°C.) | Pressure (atms) | Time (hours) | p-phenylene-diamine |
| 3 | Pd-C (5% of Pd) | 0.25 | Ethanol | 50 | 60 | 4 | 98 |
| 4 | " | 0.25 | Tetrahydrofuran | 50 | 60 | 6 | 97 |
| 5 | " | 0.01 | Ethanol | 140 | 60 | 8 | 98 |
| 6 | Stabilized nickel | 0.5 | " | 140 | 75 | 3 | 95 |
| 7 | PtO$_2$ | 0.25 | Tetrahydrofuran | 50 | 60 | 3 | 95 |
| 8 | CuO + CuCr$_2$O$_4$ | 0.5 | Ethanol | 140 | 70 | 3 | 94 |
| 9 | Ni(HCO$_2$)$_2$* | 0.5 | " | 100 | 60 | 3 | 96 |
| 10 | Raney Ni | 0.25 | " | 100 | 60 | 3 | 97 |

*Prepared by treating nickel formate with diphenyl ether at 230° C.for 2 hours.

EXAMPLE 11

Using the same apparatus and procedure as set forth in Example 3, 1.8 g of 4,4' dinitroazoxybenzene, 0.2 g of PtO$_2$ and 25 ml of ethanol were charged into the reactor, and reacted for 6 hours while introducing hydrogen at 60 atms. p-Phenylene diamine was obtained in a yield of 97%.

EXAMPLE 12

A glass reactor equipped with a stirrer and a reflux condenser was charged with 81.8 g of 4,4'-dinitroazobenzene, 120 ml of ethanol, 60 ml of water and 8 ml of 12 N conc. hydrochloric acid, and they were stirred. Then, 40 g of iron powder was added, and the reaction was carried out at 80° C. for 6 hours. After the reaction, 3.9 g of sodium hydroxide was added to the reaction mixture at room temperature, followed by filtration.

The solid matter in the filter was washed with 50 ml of anisole, and the wash liquid was added to the filtrate. Furthermore, 1.00 ml of anisole and 15 g of sodium chloride were added to separate the organic phase.

The resulting anisole-containing organic phase was distilled at reduced pressure to afford 4.3 g of a fraction having a boiling point of 173° to 180° C./30 mmHg. This fraction had a melting point of 138° C., and was identified by its IR spectrum to be p-phenylenediamine.

EXAMPLES 13 TO 16 AND COMPARATIVE EXAMPLE 1

A glass reactor equipped with a stirrer and a reflux condenser was charged with 4,4'-dinitroazobenzene, iron powder, conc. hydrochloric acid, and a solvent under the conditions shown in Table 3, and the reaction was performed at the reaction temperatures for the periods shown in Table 3.

After the reaction, sodium hydroxide was used in the same molar amount as the conc. hydrochloric acid used in the reaction. Then, the mixture was filtered. The solid matter such as iron compound was washed with alcohol. The filtrate and the wash liquid were combined, and gas-chromatographically analyzed for the determination of the resulting p-phenylenediamine. The results are shown in Table 3.

analysis of this solid shows that 4,4'-dinitroazobenzene, 4-nitroazobenzene, 4-nitroazoxybenzene, and 4,4'-dinitroazoxybenzene were obtained in a yield of 83.5%, 5%, 7%, and 1%, respectively, based on the starting azobenzene.

(B) Second step

Then, a 500 ml pressure reactor equipped with a stirrer, a pressure gauge, a thermometer and a gas-introducing tube was charged with 6.6 g of the solid obtained in the first step, 0.1 g of palladium-on-carbon (containing 5% of palladium) and 200 ml of ethanol. The air-tight inside of the reactor was purged with nitrogen, and then hydrogen at a pressure of 30 kg/cm$^2$ was introduced from the gas-introducing tube. The reaction was carried out with stirring at 50° C. for 5 hours.

After the reaction, the excess of hydrogen was released from the reactor. The reaction mixture was filtered. The solid cake was fully washed with ethanol to remove the catalyst. The filtrate and the wash liquid were combined, and distilled to afford 4.7 g of a fraction having a boiling point of 157° to 160° C./13 mmHg and a melting point of 145° to 147° C.

This fraction was identified as p-phenylenediamine as a result of analysis by IR spectrum and gas-chromatography. The gas-chromatographic analysis was carried Table 3

| Example | 4,4''-dinitroazobenzene | Iron powder | Conc. HCl (12N) | Solvent | Reaction conditions Temperature | Time (hours) | NaOH (post treatment) | Yield of p-phenylene diamine |
|---|---|---|---|---|---|---|---|---|
| 13 | 8.16 g | 50 g | 10 ml | 50% aqueous ethanol (250 ml) | 90° C. | 6 | 4.8 g | 85% |
| 14 | 8.16 | 20 | 5 | 50% aqueous ethanol (80 ml) | 90 | 4 | 2.4 | 60 |
| 15 | 8.16 | 20 | 5 | Water (80 ml) | 90 | 6 | 2.4 | 60 |
| 16 | 8.16 | 20 | 0.5 | 50% aqueous ethanol (65 ml) | 95 | 20 | 0.25 | 35 |
| Comparative Ex. 1 | 8.16 | 50 | 20 | 50% aqueous ethanol (250 ml) | 90 | 6 | 9.6 | less than 1 |

EXAMPLE 17

(A) First step

A 100 ml. glass reactor equipped with a stirrer was charged with 4.5 g of azobenzene and 25 ml of nitric acid (specific gravity 1.42), and they were reacted at 50° C. with stirring for 5 hours. The reaction mixture was filtered at room temperature, and dried to obtain 5.0 g of a solid. A gas-chromatographic analysis of the dried solid showed that 4-nitroazobenzene and 4,4'-dinitroazobenzene were obtained in a yield of 93% and 2.5%, respectively based on the azobenzene.

Then, a 200 ml glass reactor equipped with a stirrer was charged with 5.0 g of the reaction product previously obtained, 30 ml of nitric acid (specific gravity 1.42) and 30 ml of sulfuric acid (specific gravity 1.8), and they were reacted with stirring at 15° to 20° C. for 3 hours. The reaction mixture was filtered at room temperature. The cake was washed with water and dried to afford 6.6 g of a solid. A gas-chromatographic out under the following conditions.

| Filler: | Silicon SE-30 (a product of Nippon Chromato Kogyo K.K.); rate of impregnation 10% | |
|---|---|---|
| Carrier: | Diasolid L (a kind of diatomaceous earth, a product of Nippon Chromato Kogyo K.K.) | |
| Column length: | 1 m | |
| Column inside diameter: | 3 mm | |
| He flow rate: | 50 ml/min. | |
| Column temperature: | 250° C. | |
| Maintenance time: | 4-nitroazobenzene | 1 minute |
| | 4-nitroazoxybenzene | 1 minute and 50 seconds |
| | 4,4'-dinitroazobenzene | 3 minutes |
| | 4,4'-dinitroazoxybenzene | 3 minutes and 45 seconds |

EXAMPLE 18

(A) First step

A 200 ml glass reactor equipped with a stirrer was charged with 4.5 g of azobenzene, 25 ml of nitric acid (specific gravity 1.42) and 25 ml of conc. sulfuric acid (specific gravity 1.8), and the reaction was performed with stirring at 5° to 10° C. for 2 hours. After the reaction, the reaction mixture was filtered. The cake obtained was washed with water and dried to afford 6.4 g of a solid. A gas-chromatographic analysis of the solid showed that 4,4'-dinitroazobenzene and 4-nitroazoxybenzene were obtained in a yield of 40% and 31%, respectively, based on the starting azobenzene.

(B) Second step

In the same way as in Example 17, (B), 6.4 g of the solid obtained in the first step (A), 0.3 g of stabilized nickel and 200 ml of tetrahydrofuran were charged into the reactor. While hydrogen was introduced at a pressure of 80 kg/cm$^2$, the reaction was performed at 120° C. for 5 hours.

The catalyst was separated from the reaction mixture by filtration, and the residue was distilled to afford 3.4 g of a fraction having a boiling point of 156° to 160° C./13 mmHg and a melting point of 145° to 147° C. This fraction was identified as p-phenylenediamine as a result of analysis by IR spectrum and gas-chromatography.

EXAMPLE 19

(A) First step

A 100 ml glass reactor equipped with a stirrer was charged with 4.5 g of azobenzene, 10 ml of nitric acid (specific gravity 1.42) and 2 ml of conc. sulfuric acid (specific gravity 1.8), and the reaction was carried out at 40° C. for 6 hours. While maintaining the reaction mixture in the reactor at 15° to 16° C., a mixture of 5 ml of nitric acid (specific gravity 1.42) and 10 ml of sulfuric acid (specific gravity 1.8) was added with stirring. The reaction was carried out at this temperature for another 6 hours.

The product was separated by filtration, washed with water, and recrystallized from acetic acid to afford 5.3 g of orange crystals having a melting point of 222° C. From IR spectrum analysis, these crystals were identified as 4,4'-dinitroazobenzene. The yield of this product was 78.8%.

(B) Second step

In the same way as in Example 17, (B), 5.3 g of the 4,4'-dinitroazobenzene obtained in the first step above, 0.1 g of platinum oxide and 150 ml of ethanol were charged, and while introducing hydrogen at a pressure of 20 kg/cm$^2$, the reaction was carried out at 50° C. for 4 hours. The catalyst was separated by filtration from the reaction mixture, and the residue was distilled to afford 3.8 g of a fraction having a boiling point of 156° to 160° C./13 mmHg and a melting point of 145° to 147° C. This fraction was identified as p-phenylenediamine. The yield of the p-phenylenediamine was 71.2% aased on the azobenzene.

COMPARATIVE EXAMPLE 2

In the same way as in Example 19, (A), 4.5 g of azobenzene, 10 ml of nitric acid (specific gravity 1.42), and 10 ml of conc. sulfuric acid (specific gravity 1.8), and the reaction was carried out with stirring at 40° C. for 6 hours.

While maintaining the reaction mixture in the reactor at 15° to 16° C., a mixture of 5 ml of nitric acid (specific gravity 1.42) and sulfuric acid (specific gravity 1.8) was added with stirring. The reaction was carried out at this temperature for an additional 6 hours.

The reaction product was separated by filtration, washed with water, and recrystallized from acetic acid to afford 2.1 g of orange crystals of 4,4'-dinitroazobenzene. The yield of 4,4'-dinitroazobenzene was as low as 31.2%.

EXAMPLE 20

A 500 ml autoclave equipped with a stirrer and a gas-introducing tube was charged with 9.5 g of 2,4,4'-trinitroazobenzene, 0.6 g of PtO and 100 ml of ethanol. The inside of the reactor was purged completely with hydrogen, and the reaction was performed at 80° C. for 6 hours with stirring while maintaining the pressure of hydrogen at 70 kg/cm$^2$.G. The reaction mixture was filtered. The cake was washed with water. The wash liquid and the filtrate were combined, and distilled to afford 2.5 g of a fraction having a boiling point of 174° to 180° C./30 mmHg.ab. This fraction coincided with p-phenvlenediamine as a standard product. The distillation residue was recrystallized from chloroform to afford 3.2 g of 1,2,4-triaminobenzene having a melting point of 93° to 96° C. This product corresponded in IR spectrum with a standard product.

EXAMPLE 21

Azobenzene (0.9 g) was added to a mixture of 10 ml of conc. nitric acid and 10 ml of sulfuric acid under ice cooling. The mixture was heated to 25° to 27° C. cover the course of 30 minutes, and reacted at this temperature for 3 hours. After the reaction, the reaction mixture was poured into ice water. The crystals precipitated were collected and recrystallized from acetic acid. The crystals were separated by filtration, and dried to afford 1.2 g of crystals having a melting point of 168° to 170° C. These crystals corresponded in IR spectrum with a standard product of 2,4,4'-trinitroazobenzene.

EXAMPLE 22

Two-step nitration of azobenzene in an acid recycle system (A) First step (4-nitroazobenzene from azobenzene)

To 100 parts of azobenzene was added a mixture consisting of 36.6 parts of nitric acid, 96.7 parts of sulfuric acid and 91.2 parts of water, and the resulting mixture was reacted at 70° C. for 5 hours. After the reaction, the reaction mixture was cooled to room temperature, and filtered. The cake was washed with 12.4 parts of pure water and dried to afford 124.4 parts of a cake consisting of 116.0 parts of 4-nitroazobenzene, 2.7 parts of 4-nitroazoxybenzene, 1.4 parts of 4,4'-dinitroazobenzene, and small amounts of unidentifiable compounds. In 212.6 parts of the filtrate, the concentration of nitric acid was about 0% by weight, and the concentration of sulfuric acid was 45.5% by weight. The amount of water was about 54.5%.

The filtrate was distilled in a distillation still to drive off 80.4 parts of water, and to recover concentrated acids. Of 80.4 parts of the evaporated water, 39.1 parts was utilized in the next cycle of the first step, and the remainder (41.3 parts) was discarded.

(B) Second step (4,4'-dinitroazobenzene from 4-nitroazobenzene)

124.4 parts of the cake obtained in the first step was added to a mixture consisting of 202.7 parts of nitric acid, 449.9 parts of sulfuric acid and 236.6 parts of water, and the mixture was reacted at 70° C. for 5 hours. After the reaction, the reaction mixture was cooled to room temperature, and filtered. The cake was washed with 12.4 parts of pure water to obtain 158.6 parts of a cake containing a small amount of water which on analysis, was found to contain 78.7% by weight of 4,4'-dinitroazobenzene, 2.8% by weight of 4,4'-dinitroazoxybenzene and 1.5% by weight of 4-nitroazobenzene. The conversion of 4-nitroazobenzene was 98%, and the selectivity of 4,4'-dinitroazobenzene was 90.8%.

On the other hand, as the filtrate, 867.4 parts of mixed acid consisting of 19.9% by weight of nitric acid and 51.9% by weight of sulfuric acid was obtained. 1/4.7 of the mixed acid was used in the next cycle of the first step, and the remainder, combined with the acids recovered from the filtrate in the first step and 75.0 parts of 86.3 wt% nitric acid, was used in the next cycle of the second step.

(C) When the procedures (A) and (B) were repeated utilizing the filtrates obtained in the first and second steps, hardly any change was observed in the results of the reactions. Some examples are shown in Table 4.

Table 4

| | Results of the reactions | | | |
|---|---|---|---|---|
| | First step | | Second step | |
| Cycle | Conversion (%) | Selectivity of 4-nitroazo-benzene (%) | Conversion (%) | Selectivity of 4,4'-dinitro-azobenzene (%) |
| 1 | 100 | 93 | 98 | 90.8 |
| 5 | 100 | 92 | 97 | 90.0 |
| 10 | 100 | 90 | 95 | 88.5 |

EXAMPLES 23 TO 30 AND COMPARATIVE EXAMPLES 3 TO 11

Azobenzene in each of the amounts shown in Table 5 was added in portions to a mixture of conc. nitric acid and conc. sulfuric acid in each of the amounts indicated in Table 5 with stirring. The conc. nitric acid used had a specific gravity of 1.42 and a concentration of 69.8%, and the conc. sulfuric acid had a specific gravity of 1.84 and a concentration of 95.6%. The concentrations of $HNO_3$, $H_2SO_4$ and $H_2O$ in the mixed acid and the $H_2SO_4/H_2O$ weight ratio at the start of the reaction were as shown in Table 5.

For comparison, the experiment was performed using fuming nitric acid or conc. nitric acid under the conditions shown in Table 5. It is clearly seen from Comparative Example 3 that when fuming nitric acid is used, 4,4'-dinitroazobenzene and 2,4,4'-trinitroazobenzene were formed in larger amounts than 4-nitroazobenzene even at a temperature of as low as −5° C. to 0° C., and at higher temperatures, more 2,4,4'-trinitroazobenzene was formed. In particular, a comparison of Example 26 with Comparative Example 5 shows that even when the feed ratio of the reactants is the same, the use of fuming nitric acid even at low temperatures leads to the formation of unwanted azoxybenene and 4-nitroazoxybenzene. In Comparative Example 6 in which only conc. nitric acid is used, 4-nitroazobenzene can be formed, but the reaction is difficult to apply to the recycle system in accordance with this invention.

Table 5

| Example (Ex.) or Comparative Example (CEx.) | | Ex. 25 | Ex. 26 | Ex. 27 | Ex. 28 | CEx. 3 | CEx. 4 | CEx. 5 | CEx. 6 | CEx. 7 | CEx. 8 |
|---|---|---|---|---|---|---|---|---|---|---|---|
| Amounts charged | Azo (g) | 3.6 | 2.7 | 1.8 | 1.8 | 0.9 | 0.9 | 2.7 | 0.45 | 1.8 | 1.8 |
| | $HNO_3$ (ml) | 4.0 | 4.0 | 4.0 | 2.0 | 10 (fuming) | 10 (fuming) | 5 (fuming) | 5 | 0.45 | 0.45 |
| | $H_2SO_4$ (ml) | 2.0 | 1.0 | 1.0 | 1.5 | — | — | — | — | 3.0 | 3.0 |
| | $H_2O$ (ml) | — | — | — | — | — | — | — | — | 1.0 | 1.0 |
| Concentration (%) | $HNO_3$ | 42.7 | 52.9 | 52.9 | 35.7 | 94.1 | 94.1 | 94.1 | 69.8 | 8.4 | 8.4 |
| | $H_2SO_4$ | 33.7 | 21.0 | 21.0 | 42.3 | — | — | — | — | 66.2 | 66.2 |
| | $H_2O$ | 23.6 | 26.2 | 26.2 | 22.0 | 5.9 | 5.9 | 5.9 | 30.2 | 25.4 | 25.4 |
| $H_2SO_4/H_2O$ weight ratio | | 1.45 | 0.8 | 0.8 | 1.93 | — | — | — | — | 3.7 | 3.7 |
| Reaction temperature (°C.) | | 50 | 40 | 40 | 50 | −5—0 | 10 | 0 − 2 | 80 | 90 | 20 |
| Reaction time (hours) | | 4 | 4 | 4 | 4 | 4.5 (min.) | 1.5 | 5 | 2 | 5 | 5 |
| Yield (%) | 4-Azo | 80 | 92 | 90 | 65 | | | 30 | 70 | 15 | 10 |
| | 4,4'-Azo | 10 | | | | 30 | | 5 | 5 | | |
| | 2,4,4'-Azo | | | | | 25 | 85 | | | | |
| | 4-Azoxy | | 2 | | 13 | 20 | | 25 | 20 | | |
| | Azo | | 5 | 8 | 10 | | | 15 | | 70 | 90 |
| | Azoxy | 8 | | | 10 | | | 10 | | 10 | |

| Example (Ex.) or Comparative Example (CEx.) | | CEx. 9 | CEx. 10 | CEx. 11 | Ex. 29 | Ex. 30 | Ex. 31 | Ex. 32 |
|---|---|---|---|---|---|---|---|---|
| Amounts charged | Azo (g) | 3.6 | 0.9 | 1.8 | 1.8 | 1.8 | 1.2 | 5.4 |
| | $HNO_3$ (ml) | 4.0 | 0.3 | 0.45 | 0.45 | 0.65 | 0.45 | 2.2 |
| | $H_2SO_4$ (ml) | 2.0 | 5.4 | 3.0 | 2.0 | 2.0 | 1.5 | 2.0 |
| | $H_2O$ (ml) | — | 3.1 | — | — | 1.0 | 1.0 | — |
| Concentration (%) | $HNO_3$ | 42.7 | 2.3 | 7.2 | 10.3 | 11.5 | 10.2 | 32.2 |
| | $H_2SO_4$ | 33.7 | 73.6 | 85.7 | 81.4 | 62.8 | 60.4 | 51.8 |
| | $H_2O$ | 23.6 | 24.1 | 7.1 | 8.3 | 25.7 | 29.4 | 16.0 |
| $H_2SO_4/H_2O$ weight ratio | | 1.45 | 2.6 | 12.0 | 9.9 | 2.44 | 2.0 | 3.2 |
| Reaction temperature (°C.) | | 20 | 0 - 2 | 50 | 50 | 40 | 70 | 50 |
| Reaction time (hours) | | 5 | 2 | 5 | 4 | 5.5 | 5 | 5 |
| | 4-Azo | 45 | | 50 | 70 | 80 | 75 | 75 |

Table 5-continued

|  |  |  |  |  |  |  |  |
|---|---|---|---|---|---|---|---|
| Yield (%) | 4,4'-Azo |  |  |  |  |  | 5 |
|  | 2,4,4'-Azo |  |  |  |  |  |  |
|  | 4-Azoxy |  |  |  | 10 |  | 10 |
|  | Azo | 50 | 98 | 45 | 10 | 15 | 10 |
|  | Azoxy |  |  | 5 | 7 | 3 | 15 | 5 |

(1) HNO₃: Specific gravity 1.42 (69.8%)
(2) H₂SO₄: Specific gravity 1.84 (95.6%)
(3) Azo: Azobenzene
4-Azo: 4-Nitroazobenzene
4,4'-Azo: 4,4'-Dinitroazobenzene
2,4,4'-Azo: 2,4,4'-trinitroazobenzene
4-Azoxy: 4-Nitroazoxybenzene
Azoxy: Azoxybenzene

EXAMPLES 33 TO 35 AND COMPARATIVE EXAMPLES 12 TO 15

Under the conditions shown in Table 6, 4-nitroazobenzene was reacted with mixed acid or fuming nitric acid. The results are shown in Table 6. The abbreviations in Table 6 are the same as the footnote to Table 5.

Table 6

| Example (Ex.) or Comparative Example (CEx.) |  | Ex. 33 | Ex. 34 | Ex. 35 | CEx. 12 | CEx. 13 | CEx. 14 | CEx. 15 |
|---|---|---|---|---|---|---|---|---|
| Amount charged | Axo (g) | 0.45 | 0.45 | 0.45 | 0.45 | 0.45 | 0.9 | 0.9 |
|  | HNO₃ (ml) | 4.0 | 4.0 | 5.0 | 5.0 | 5.0 | 4.0 | 4.0 |
|  | H₂SO₄ (ml) | 2.0 | 2.0 | 2.0 | 1.0 | 2.0 | — | 4.0 |
|  | H₂O | — | — | — | — | — | — | — |
| Concentration (%) | HNO₃ | 42.6 | 42.6 | 46.3 | 55.7 | 46.3 | 69.8 | 30.8 |
|  | H₂SO₄ | 33.6 | 33.6 | 29.2 | 17.6 | 29.2 | — | 48.6 |
|  | H₂O | 23.8 | 23.8 | 24.5 | 26.7 | 24.5 | 30.2 | 20.6 |
| H₂SO₄/H₂O weight ratio |  | 1.41 | 1.41 | 1.19 | 0.66 | 1.19 | — | 2.46 |
| Reaction temperature (°C.) |  | 50 | 25 | 50 | 50 | 25 | 98 | 50 |
| Reaction time (hours) |  | 4 | 4 | 4 | 4 | 4 | 6 | 4 |
| Yield (T) | 4,4'-Azo | 90 | 62 | 72 | 48 | 22 | 80 | 8 |
|  | 2,4,4'-Azo |  |  |  |  |  |  |  |
|  | 4-Azo | 10 | 38 | 28 | 30 | 57 | 20 |  |
|  | 4-Azoxy |  |  |  |  | 18 |  |  |

What we claim is:

1. A process for preparing a compound of the formula wherein m represents zero or 1, which comprises reacting azobenzene with nitric acid in the presence of sulfuric acid in two steps, wherein (1) the first-step reaction is carried out under the following conditions $0 < x \leq 80$, $0 < y \leq 11$, and $-0.3x + 12 \leq y \leq -0.22x + 22$ wherein x is the reaction temperature in °C., and y is the weight ratio of sulfuric acid to water fed into the reaction system, and (2) the second-step reaction is carried out under the following conditions $0 \leq x$, and $(1.7/100)x + 1.7 \leq y \leq -(3.9/88)x + 3.9$.

2. The process of claim 1 wherein in the first step, the mole ratio of nitric acid to azobenzene (HNO₃/azobenzene) fed into the reaction system is 1.5−0.5, and in the second step, the moles ($M_1$) of nitric acid, the moles ($M_2$) of mononitroazobenzene, and the moles ($M_3$) of the unreacted azobenzene are in the following relation $1 \leq M_1/(M_2 + 2M_3) \leq 50$.

3. The process of claim 1 wherein the first step reaction is carried out under the following conditions $0 < x \leq 80$, $0 < y \leq 3$, $-7.3x + 12 \leq y \leq -0.22x + 22$, and $0.7 \leq HNO_3/azobenzene\ (mole\ ratio) \leq 1.2$, and the second-step reaction is carried out under the following conditions $3 \leq M_1/(M_2 + 2M_3) \leq 30$.

4. The process of claim 2 or 3 which comprises a first step of preparing 4-nitroazobenzene by reacting azobenzene with nitric acid in the presence of sulfuric acid and separating the resulting solid 4-nitroazobenzene from the acid, a second step of forming the compound of the formula by reacting 4-nitroazobenzene formed in the first step with nitric acid in the presence of sulfuric acid, and a third step of separating and recovering the solid compound of the formula formed in the second step, wherein a part of the mixed acid left after the separation and recovery of the compound of the formula in the third step is used in the nitration reaction of azobenzene in the first step, and the remainder is used for the nitration of 4-nitroazobenzene in the second step; the residual liquid separated in the first step which consists of sulfuric acid and is diluted with water generated from the nitration reaction is concentrated; and the concentrated sulfuric acid, fresh nitric acid, and the mixed acid used for the second-step nitration are mixed, after which the resulting mixed acid is reacted with 4-nitrobenzene in the second step.

5. The process of claim 4 wherein the entire process is carried out without substantially discharging the spent acids out of the system.

* * * * *